(12) United States Patent
Köhrer

(10) Patent No.: US 11,911,232 B2
(45) Date of Patent: Feb. 27, 2024

(54) CONTAINER FOR STORING A DENTAL, ESPECIALLY ENDODONTIC INSTRUMENT, KIT AND METHOD

(71) Applicant: Dennis Manuel Köhrer, Neuss (DE)

(72) Inventor: Dennis Manuel Köhrer, Neuss (DE)

( * ) Notice: Subject to any disclaimer, the term of this patent is extended or adjusted under 35 U.S.C. 154(b) by 611 days.

(21) Appl. No.: 16/944,636

(22) Filed: Jul. 31, 2020

(65) Prior Publication Data

US 2022/0031438 A1 Feb. 3, 2022

(51) Int. Cl.
*A61C 19/02* (2006.01)
*A61C 5/42* (2017.01)
*A61L 2/20* (2006.01)

(52) U.S. Cl.
CPC .............. *A61C 19/02* (2013.01); *A61L 2/206* (2013.01); *A61L 2/208* (2013.01); *A61C 5/42* (2017.02); *A61C 2202/00* (2013.01); *A61L 2202/123* (2013.01); *A61L 2202/24* (2013.01)

(58) Field of Classification Search
CPC ....... A61C 19/02; A61C 5/42; A61C 2202/00; A61L 2/206; A61L 2/208; A61L 2202/123; A61L 2202/24
USPC .................................. 206/368; 433/224, 81
See application file for complete search history.

(56) References Cited

U.S. PATENT DOCUMENTS

| | | | |
|---|---|---|---|
| 4,165,562 A | 8/1979 | Sarfatti | |
| 4,867,305 A * | 9/1989 | Schneider | A61C 1/145 206/230 |
| 5,593,391 A * | 1/1997 | Stanners | A61M 5/322 604/110 |
| 5,967,778 A | 10/1999 | Riitano | |
| 8,714,354 B2 * | 5/2014 | Cheetham | A61C 5/66 206/368 |
| 8,827,702 B2 * | 9/2014 | Mamraev | A61C 8/0087 433/163 |
| 9,597,092 B2 | 3/2017 | Pernot et al. | |
| 10,398,523 B2 * | 9/2019 | Roesler | A61C 8/0087 |
| 2006/0223035 A1 | 10/2006 | Fischer | |
| 2011/0171595 A1 * | 7/2011 | Turner | A61C 1/08 433/127 |
| 2011/0244419 A1 | 10/2011 | Tofft | |

(Continued)

FOREIGN PATENT DOCUMENTS

| | | |
|---|---|---|
| DE | 10146905 A1 | 7/2003 |
| EP | 1417937 A1 | 5/2004 |
| JP | H06321268 A | 11/1994 |

*Primary Examiner* — J. Gregory Pickett
*Assistant Examiner* — Jenine Pagan
(74) *Attorney, Agent, or Firm* — Calderon, Safran & Cole P.C.

(57) ABSTRACT

The present invention relates to a kit comprising
an endodontic instrument in the form of an endodontic file and
a container with a lower container part, for receiving the working section (3c) of the endodontic instrument, and an upper container part, for receiving the upper axial end region of the instrument,
wherein a holder is provided on the upper side of the lower container part, which holder comprises an axial through-opening through which the working section of the instrument is inserted into the lower container part and in which the instrument, in particular the tool shaft of the instrument, is fixed in a clamping manner,
wherein the upper container part is connected with the lower container part in an airtight manner to form the container, and the interior of the container and the instrument are sterile.

17 Claims, 11 Drawing Sheets

(56) References Cited

U.S. PATENT DOCUMENTS

| | | | | |
|---|---|---|---|---|
| 2014/0163555 A1* | 6/2014 | Pernot | ............... | A61C 1/14 |
| | | | | 606/80 |
| 2014/0311932 A1* | 10/2014 | Sakaguchi | ........... | A61C 8/0087 |
| | | | | 206/368 |
| 2019/0117335 A1* | 4/2019 | Langbein | ............. | A61C 19/042 |
| 2019/0159874 A1* | 5/2019 | Jung | ............... | B65D 81/28 |

* cited by examiner

CONTAINER FOR STORING A DENTAL, ESPECIALLY ENDODONTIC INSTRUMENT, KIT AND METHOD

FIELD OF THE INVENTION

The present invention relates to a kit for a single endodontic instrument in the form of an endodontic file, which has a tool shaft, on one upper axial end region of which tool shaft a handle or a coupling section for connection to a motor-driven rotary tool is formed and on the other, lower end region of which tool shaft an in particular conically tapered working section is formed, and a container formed as a disposable package for storing a single endodontic instrument. Furthermore, the invention relates to a method for storing an endodontic instrument.

BACKGROUND OF THE INVENTION

In the field of endodontics, root canal treatment is one of the most important topics. In dentistry, root canal treatment is understood to be a therapy with the aim of preserving a tooth, whose pulp is vital but irreversibly inflamed our devitalized, i.e. dead. During the root canal treatment, the vital or devitalized pulp tissue is removed from the root canal and the root canal is expanded. Therein, the infected root dentin surrounding the root canal is also removed by being filed out. For this purpose, special endodontic instruments such as endodontic files or endodontic drills are used. These have a tool shaft, on one upper axial end region of which tool shaft a handle or a coupling section for connection to a motor-driven rotary tool is formed and on the other lower end region of which an in particular conically tapered working section is formed. This working section usually has a diameter of only a few tenths of a millimeter and is designed flexibly, so that it can adapt to the shape of the root canal to be treated.

Such endodontic instruments are currently delivered unsterilized by the manufacturer and must therefore be extensively sterilized in the dentist's practice before use. As a rule, sterilization is therefore only carried out shortly before the root canal treatment. The instruments are then stored together, which entails the risk of mutual contamination. Handling the endodontic instruments also proves to be difficult during treatment, in particular when the endodontic instruments have to be gripped at their thin and flexible shaft and possibly have to be inserted into a rotating tool with their coupling section without contaminating the working section.

SUMMARY OF THE INVENTION

Against this background, it is a task of the invention to specify a kit of the type mentioned above, which makes it possible to store an endodontic instrument in an easy and safe manner in a sterile environment for transport. Furthermore, a corresponding method shall be specified.

For this purpose, the invention proposes a kit comprising a single endodontic instrument in the form of an endodontic file, which has a tool shaft, on one upper axial end region of which tool shaft a handle or a coupling section for connection to a motor-driven rotary tool is formed and on the other, lower end region of which tool shaft an in particular conically tapered working section is formed, and a container that is designed as a disposable packaging for storing a single endodontic instrument and has a lower container part, which is open at its top side for receiving the working section of the instrument, and has an upper container part, which is open at its underside for receiving the upper axial end region of the instrument, wherein a holder is provided on the upper side of the lower container part, which holder has an axial through-opening through which the working section of the instrument is inserted into the lower container part and in which through-hole the instrument, in particular the tool shaft of the instrument, is positioned radially and/or axially and is fixed in a clamping manner and/or by a latching connection, wherein the upper container part is connected to the lower container part in an airtight manner to form the container, and wherein the interior of the container and the instrument are sterile, and wherein at least the lower container part consists of a dimensionally stable material in such a way that the instrument that is inserted into the lower container part and positioned in the holder can be gripped at its upper end region and pulled out of the lower container part while being held manually without the lower container part being deformed by the holding pressure to such an extent that it comes into contact with the working section.

Furthermore, to solve the task, a method for storing an endodontic instrument is provided, in which the instrument is provided in a kit according to the invention.

The invention is thus based on the consideration of using a tubular container for packaging an endodontic file, which can be designed as a hand file or a rotating file, the tubular container having an upper container part and a lower container part and being made of a material that is dimensionally stable, for example in comparison with blisters. The division of the container into the lower container part and the upper container part is provided in such a way, that the lower working section of an endodontic instrument can be accommodated in the lower container part and the upper end region of the endodontic instrument with the handle or the coupling section for connection to a rotating and/or rotary tool can be accommodated in the upper container part. The endodontic instrument is positioned in the lower container part by means of a holder, which is provided at the upper end area of the lower container part and comprises a central through-opening for the tool shaft of the endodontic instrument. The arrangement is configured such, that the endodontic instrument remains in the holder, when the upper container part is detached from the lower container part. The holder is designed to fix the endodontic instrument inserted to it in a clamping/latching manner and to align it radially and/or axially, for which purpose the holder is expediently made from an elastic plastic material. In this way, the working section is protected by the lower container part when the endodontic instrument is gripped or is coupled with a motor-driven tool at its upper end region, before the working section of the endodontic instrument is pulled out of the lower container part for the actual treatment. Since the lower container part is made of a comparatively stable material, which does not deform or deforms only imperceptibly when the lower container part is gripped, it is particularly easy to insert the coupling part into a corresponding coupling section of a rotating and/or oscillating tool.

Preferably, the upper container part is made of the same material as the lower container part or of a material with similar dimensional stability. However, the upper container part can also be softer, if its function is only to close the container.

Expediently, the lower container part and/or upper container part are made of a plastic material, in particular a crystal clear plastic material, so that the container can be easily manufactured. The container can have a magnifying area or a lens area, such that the working section can be distinctively examined from the outside.

According to a preferred embodiment of the invention, it is provided that the lower container part and/or the upper container part is made of a material transparent to sterilizing radiation. In this case, it is possible to sterilize the kit consisting of the container and the endodontic instrument positioned therein by exposing the kit to a sterilizing radiation from the outside. For example, the kit can be exposed to ionizing radiation, in particular with UV, X-ray, gamma or electron radiation in order to be sterilized. Further, the upper container part and/or the lower container part can consist of a material, which is transparent to a sterilization gas, in particular to ethylene oxide. This way, the packaged products can be sterilized by gas after having been closed and packed.

In a further embodiment of the invention it is intended that the lower container part and/or the upper container part has an opening, which is closed by a sterilising membrane. The opening can be pierced in order to introduce a gaseous or vaporous fluid, in particular hydrogen peroxide, peracetic acid and/or dissolved ozone into the container, wherein the sterilising membrane is self-closing after removal of the needle. In this case, a gaseous and/or vaporous fluid, such as for example hydrogen peroxide, peracetic acid and/or dissolved ozone can be introduced into the lower container part and/or the upper container part, for which purpose the corresponding sterilization membrane is pierced. The sterilizing membrane therein is self-closing, so that the piercing opening of the needle closes itself again after the needle is pulled out. This design is particularly useful, if an endodontic instrument is to be reused after cleaning. The sterilization membrane can also be designed in such a way that it is permeable for the vaporous or gaseous sterilization fluid (e.g. such rated steam and air) at the high temperatures prevailing during sterilization in autoclaves, usually >121° C., but is self-closing at room temperature.

Expediently, the upper container part and the lower container part can be plugged together, wherein the arrangement is preferably designed such, that the container is sealed to be airtight when plugged together. Therein, the lower container part and the upper container part can be equipped with means for forming a groove/tongue-latching connection. Alternatively/additionally, sealing strips may be provided to seal a gap between the lower container part and the upper container part in the transition area between the lower container part and the upper container part and/or the connection between the lower container part and the upper container part can be sealed.

Another preferred design of the container according to the invention is characterized in that it is designed for storing an endodontic instrument, which has a tool shaft or a coupling section, which consists of or comprises a shaft according to DIN EN ISO 6360-1, in particular an FG-shaft or an elbow shaft or a hand piece shaft according to DIN EN ISO 6360-1.

According to an embodiment of the invention, it is provided that fastening means, in particular a threat or parts of a bayonet lock are formed on the outside of the container in order to fix the container in a receptacle of a holding box or a setting box. This embodiment is based on the consideration that the container can be designed in order to be positioned in a holding box for storage or on the dentist's chair. For this purpose, fastening means are provided in order to fix it in a receptacle of such a holding box. Such fixing can be achieved in a clamping manner. Expediently, however, the container is provided with a threat on the outside, by which it can be screwed into a receptacle provided with a corresponding counter threat. Alternatively, a bayonet lock can be used. In this case, the parts of the bayonet lock are formed at the outside of the container and the corresponding counter parts are formed on the holding box. Further, the lower container part and the upper container part can be equipped with means for forming a groove/tongue-latching connection.

In a preferred variant of the container according to the invention, it is provided that the container is equipped with a transmitting and/or receiving device. Such a device is then in particular designed and/or arranged and/or used for the automatic and/or contactless identification and/or localization and/or organisation.

Expediently, the transmitting and/or receiving device is designed and/or arranged to transmit and/or receive information preferably about an endodontic instrument, which is accommodated or can be accommodated by the container, in particular wirelessly.

If a transmitting and/or receiving device is provided, it is preferably fixed to the container, in particular on the inside. A transmitting and/or receiving device can also be at least partially incorporated or embedded into the container, in particular in a wall of the upper container part and/or the lower container part.

For example, a transmitting and/or receiving device may include or be provided by a RFID-chip and/or an RFID-transponder (RFID herein is the abbreviation for radio frequency identification system).

Furthermore, a transmitting and/or receiving device is preferably designed and/or configured in such a way that information is stored or can be stored in it, in particular on a storage medium thereof, in particular information about an endodontic instrument that is received or to be received by the container, such as for example one or more identifier thereof, a date on which sterilization of the instrument has taken place and/or other information.

Information or data stored on a transmitting and/or receiving device can be read out by means of a suitable receiver device and/or a suitable reader device. If a container or a kit according to the invention, which comprises a transmitting and/or receiving device is used together with a setting box that in particular serves as a sorting box, a receiver device or a reader device can be provided on the setting box and in particular be installed into it.

The writing of data or information to the transmitting and/or receiving device can be done preferably wirelessly by means of a suitable writing device. A reading and writing device can also be used to both read and write the data-preferably wirelessly.

Information or data read out with a receiver device or a reader device can be passed on—preferably automatically—to a management system/program (praxis management program, merchandise management system). This enables a precise, automated control, inventory and ordering. In combination with patient and treatment data it is further possible to ensure a traceability and patient or treatment and/or operation allocation.

A transmitting and/or receiving device of a container or a kit according to the invention can also contain information for the batch documentation (lot-number) of a dental instrument that is received or can be received in the container. A management system can use the sterilization and/or the expiration dates to warn against the use of expired instruments. Further, it is used in the manufacturing and production area for integration into an ERP (enterprise resource planning) software system.

As a result, advantages for the merchandise management systems as well as the ERP systems can be achieved and a reliable traceability of medical devices can be achieved.

In a further variant of the kit according to the invention it is provided that means for determining the state of use and/or the degree of wear of the working portion of an endodontic instrument, which working portion is inserted into the lower container part, are provided on the lower container part and/or the holder, wherein the means are in particular designed to determine at least one physical property of the working section.

An advantageous design of this variant is characterized in that the means for determining the state of use and/or degree of wear of the working portion are designed to determine the electrical conductivity/resistance of the working section, which means comprise electrical contacts, which are in electrical contact with a working section inserted into the lower container part at an upper or a lower end region thereof and which are connected or can be connected to the display unit, wherein the electrical contacts are in particular provided in the lower end region of the lower container part and on the underside of a stop flange of the lower container part, and wherein preferably two upper electrical contacts and two lower electrical contacts are provided on the lower container part, which electrical contacts are in electrical contact with the working section.

Therein, one pair formed by one upper and one lower contact is used for connecting the display unit and the other pair can be used for connecting a reference-measurement-circuit or a circuit for reducing the current through the working section.

This design is based on the underlying consideration of creating a possibility to determine the condition of use/degree of wear of the working section of the endodontic instrument even during treatment, in order to replace the endodontic instrument if necessary. In this way, undesirable fractures of the endodontic files can be avoided.

It has been shown that with increasing wear in particular the physical properties of the working section change. In particular, dislocations in the material stature can occur, which amongst others may result in a change of the electrical conductivity or the electrical resistance. Accordingly, in a preferred manner the electrical conductivity/electrical resistance of the working section is used to determine the condition of use/degree of wear of the working section. For this purpose, electrical contacts are provided at the lower container part, which are connected to the working section in an electrically conductive manner, when the working section is inserted into the lower container part and which electrical contacts can be tapped from the outside to determine the electrical conductivity/resistance of the working section. In praxis, the lower container part with the endodontic instrument inserted may, for example, be inserted into a measuring device, which comprises electrical transducers that, when inserted, automatically come into contact with the electrical contacts of the lower container part and form part of an electrical circuit with an energy source and a display. When the lower container part is inserted, the electrical circuit becomes closed, so that electrical current flows through the working section, the intensity of the electrical current varying according to the electrical resistance/electrical conductivity of the working section. A display can then, for example, indicate the condition of use by means of colored LEDs.

In a preferred design it is provided, that a holder is designed to fix a tool shaft of an endodontic instrument in the lower container part by means of a latching connection, wherein the tool shaft has a circumferential latching groove, with which latching means in the form of an annular latching tongue or a plurality of latching tongues provided along the circumference of the lower container part are in latching engagement, wherein the latching means preferably touch the tool shaft, are designed to be electrically conductive and are electrically connected to the upper electrical contact.

With this design, the latching tongues come into electrically conductive contact with the working section, when the working section is inserted into the lower container part as intended. In the lower region of the lower container part, an electrically conductive membrane, foil or similar may be fixed, which is in contact with the lower electrical contact and is contacted by the tip of the working section, when it is inserted into the lower container part. The electrically conductive foil/membrane, the electrically conductive tape or the like may be elastic in order to be deformed, when the working section is inserted into the lower container part. The elasticity ensures on one hand continuous contact between the tip of the working section and the foil and on the other allows for working sections of different lengths to be inserted into the lower container part provided the foil is suitably positioned.

Particularly preferably, the endodontic instrument has a tool shaft or coupling section, which consists of or comprises a shaft according to DIN EN ISO 6360-1, in particular an FG-shaft or an angle piece shaft or a hand piece shaft according to DIN EN ISO 6360-1. In this case, the endodontic instrument is compatible with associated motor-driven rotary tools.

The DIN EN ISO 6360-1 classifies shaft kinds for dental instruments, in particular rotating, i.e. rotationally driven dental instruments. Therein, the standard describes the shafts with a three-digit code (XXX), wherein the first two of the three digits describe the shaft type and the shaft diameter (for example 10=handpiece shaft with a diameter of 2.35 mm; 20=angle-piece shaft with a diameter of 2.35 mm, 31=FG shaft with a diameter of 1.60 mm). The last digit of the code describes the qualitative length ratio of identical shaft types to one another (for example: 2=very short, 3=short, 5=average, 5=long, 6=extra-long).

For example, an elbow shaft of normal length is named with the code 204 according to the standard that describes the shafts with a three-digit code (XXX), wherein the first two of the three digits describe the shaft type and the shaft diameter (for example 10=handpiece shaft with a diameter of 2.35 mm; 20=angle-piece shaft with a diameter of 2.35 mm, 31=FG shaft with a diameter of 1.60 mm).

The last digit of the code describes the qualitative length ratio of identical shaft types to one another (for example: 2=very short, 3=short, 5=average, 5=long, 6=extra-long). Longer instrument shafts can then have the code 205 or 206.

As far as types of shafts are concerned, a distinction is usually made between FG-shafts, angle-piece shafts and handpiece shafts.

Therein FG stands for the English term friction grip. An FG-shaft is usually smooth and usually has a standardized diameter of 1.6 mm. FG-shafts in particular fit into dental turbines and preferably high-speed angle-piece heads.

It goes without saying that the instruments can have different overall lengths for example a comparatively short one of 16 mm, a normal one or a long one up to an extra-long one of for example 25 mm.

Angle-piece shafts are also known as RA-shafts, wherein RA is the abbreviation for right angle. Angle-piece shafts are usually locked manually with the head of the angle-piece handpiece and may have a notch at the end of the shaft for this purpose. RA-shafts preferably have a diameter in the region of 2.2 to 2.5 mm, especially of 2.35 mm, and a total length in the range of 22 mm to 34 mm.

Handpiece shafts (or HP-shafts, where HP stands for handpiece) can also preferably have the diameter in the range of 2.2 to 2.5 mm, especially of 2.35 mm and are preferably between 34 mm and 70 mm long. As a rule, they do not have a notch; they can for example be fastened by means of a chuck in the handpiece.

According to a further variant of the method according to the invention, it is provided that a plurality of kits containing different endodontic instruments in the form of endodontic files are placed in a setting box, in which adjacent receptacles are provided, in which the containers of the kits are inserted, in particular parallel to one another.

Therein, the containers can be fixed in the receptacles of the setting box in a clamping manner, wherein in particular the setting box in the region of the receptacles and/or the lower container parts inserted into the receptacles have an elasticity, which enables such a fixation in a clamping manner.

In a preferred manner, the lower container parts are tapered towards their free ends, wherein the receptacles are preferably tapered with a corresponding conicity.

A particularly preferred variant of the method according to the invention is characterized in that kits are used, the containers of which are provided with optical markings on their top side, which optical markings correspond to the type and/or size of the endodontic instruments stored therein and/or in the region of the receptacles of the setting box optical markings are provided, which correspond to the type and/or size of the endodontic instruments stored therein.

Preferably, it is provided that after an endodontic treatment has been carried out and a number of kits have been correspondingly removed from the setting box, the setting box is photographed, by means of a recognition software it is recognized, from which receptacles of the setting box the kits have been removed and it is recognized by means of the optical markings associated with the empty receptacles, of which type and size the removed endodontic instruments are, and that the recorded data is thus processed.

Preferably, the recorded data is fed to a merchandise management and/or goods ordering system and/or a reordering of the missing kits is automatically carried out on the basis of the data.

The inventive rigidity of the containers for storing the endodontic instruments makes it possible to store these containers in a setting box, which is then provided with corresponding receptacles, in which the containers can be positioned next to each other in an upright position. For example, the tray can have a foam insert in which the receptacles are provided. Foam material is usually relatively elastic and has a high coefficient of friction, so that the containers can be safely placed and held in the receptacles.

The rigid design of the containers further allows for providing optical markings at the top side of the container, which correspond to the type and/or size of the endodontic instrument stored therein. As there is more space available on the container than on the delicate endodontic instruments themselves, the doctor/dentist can easily identify the correct instrument. In the same way, the receptacles of the setting box can be provided with appropriate optical markings, so that it is clearly defined, which type and/or size of endodontic instruments is to be accommodated in a receptacle. Because of the easy recognition of the optical markings on the receptacle and the setting box, an easy assignment is possible. Further, the optical markings on the setting box make it possible to automatically recognize, which dental, in particular endodontic instruments, are missing from the tray after a treatment. It is therefore sufficient, to take a photograph of the setting tray after use to identify which instruments have been removed from the tray by means of the optical markings assigned to the empty receptacles. The corresponding data can be fed into an accounting software. Further, it is possible, to feed it into a merchandise management and/or ordering system, so that automatic reordering and taking an inventory is possible.

With the method according to the invention it can alternatively or additionally be provided, that kits are used, the containers of which are provided with an optical marking and the setting box of which has optical markings, it can be provided that kits are used, the containers of which are each equipped with a transmitting and/or receiving device which is preferably designed and/or arranged to transmit and/or receive and in particular save information or data or signals, in particular via an endodontic instrument that is received or can be received in the container, preferably wirelessly.

In this case, it can be provided that the setting box is equipped with a reader device, which can read information or data stored on the transmitting and receiving devices.

Information or data read out by a reader device can then be fed—preferably automatically—into a merchandise management and/or goods ordering system.

This also enables an accurate and automated control, inventory and ordering/stock taking. In combination with patient and treatment data it is also possible to ensure a traceability and an allocation of patient or treatment and/or operation.

BRIEF DESCRIPTION OF THE DRAWINGS

With regard to further embodiments of the present invention, reference is made to the following design examples with reference to the enclosed drawings. The drawings show.

DETAILED DESCRIPTION OF THE PREFERRED EMBODIMENT(S)

Figure 1:
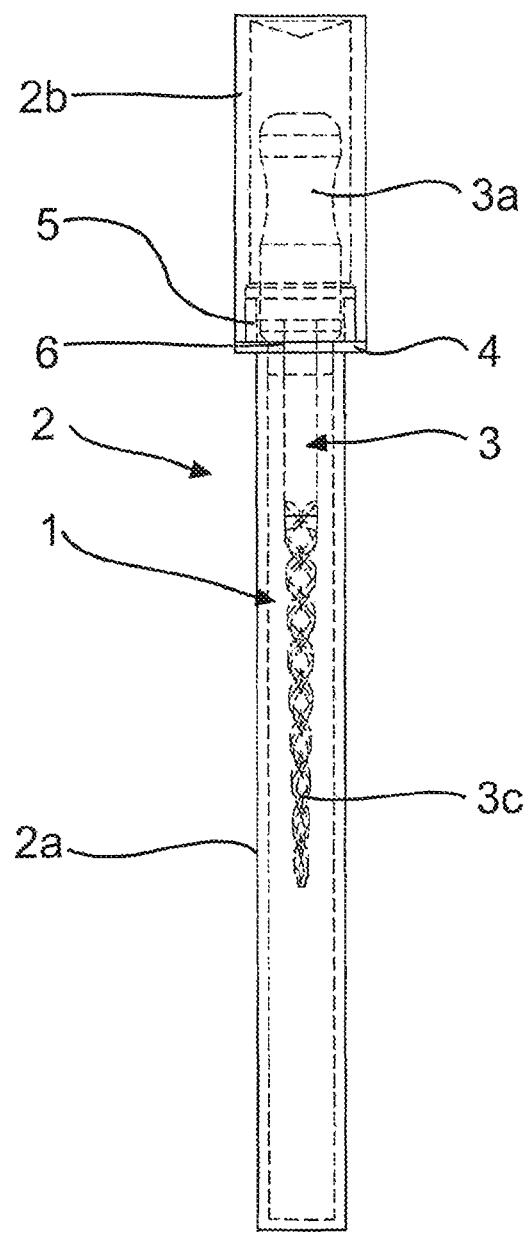
FIG. 1 a first embodiment of a kit according to the invention comprising an endodontic instrument in the form of an endodontic file, which is housed in a container formed according to the invention, in a front view, FIG. 2 the kit according to FIG. 1 with removed upper container part and an endodontic instrument partially pulled out of the lower container part, FIG. 3 the upper container part of the kit from FIG. 2, FIG. 4 a second embodiment of a kit according to the present invention with a removed upper container part, wherein the endodontic instrument is designed for coupling with a rotary-driven tool, FIG. 5 the upper container part of the kit according to FIG. 4, FIG. 6 the kit from FIG. 4, wherein the endodontic instrument is partially pulled out of the lower container part, FIG. 7 the process of inserting the endodontic instrument shown in FIG. 4 into a driven rotary tool, FIG. 8 a setting box according to the present invention for accommodating the kits according to the invention, FIG. 9 a third embodiment of the kit according to the present invention with an endodontic instrument in the shape of an endodontic file, which has a working section with a coupling section comprising a DIN-threat, FIG. 10 a fourth embodiment of a kit according to the present invention with an inserted endodontic file, FIG. 11 a plurality of kits according to the present invention that are inserted into the receptacles of a holder, FIG. 12 a kit according to the present invention inserted into a holder in enlarged view and FIG. 13 a holder for a kit according to the present invention in an enlarged view.
Figures 2, 3:
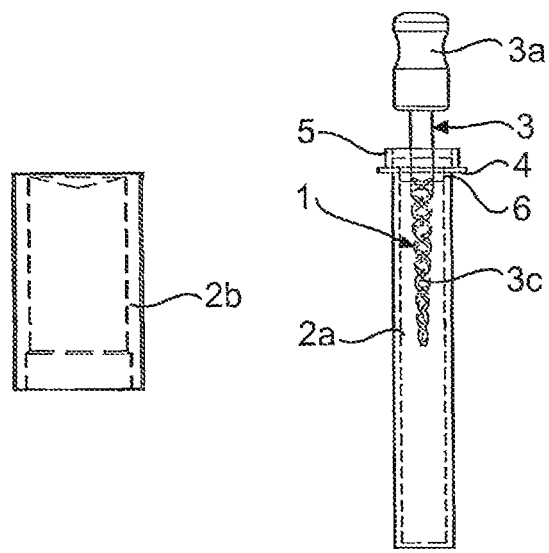
Figure 4:
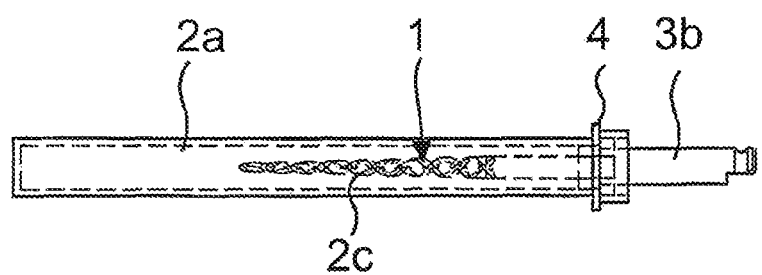
Figure 5:
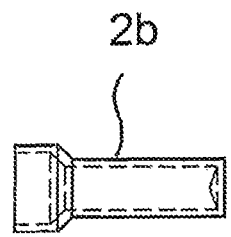
Figure 6:
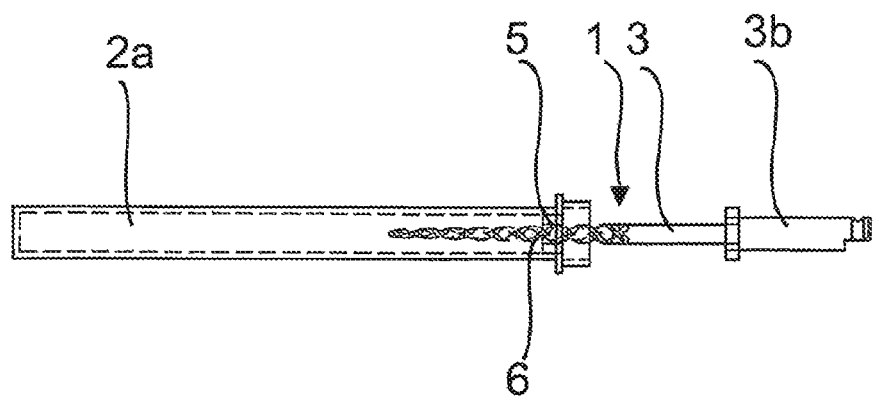
Figure 7:
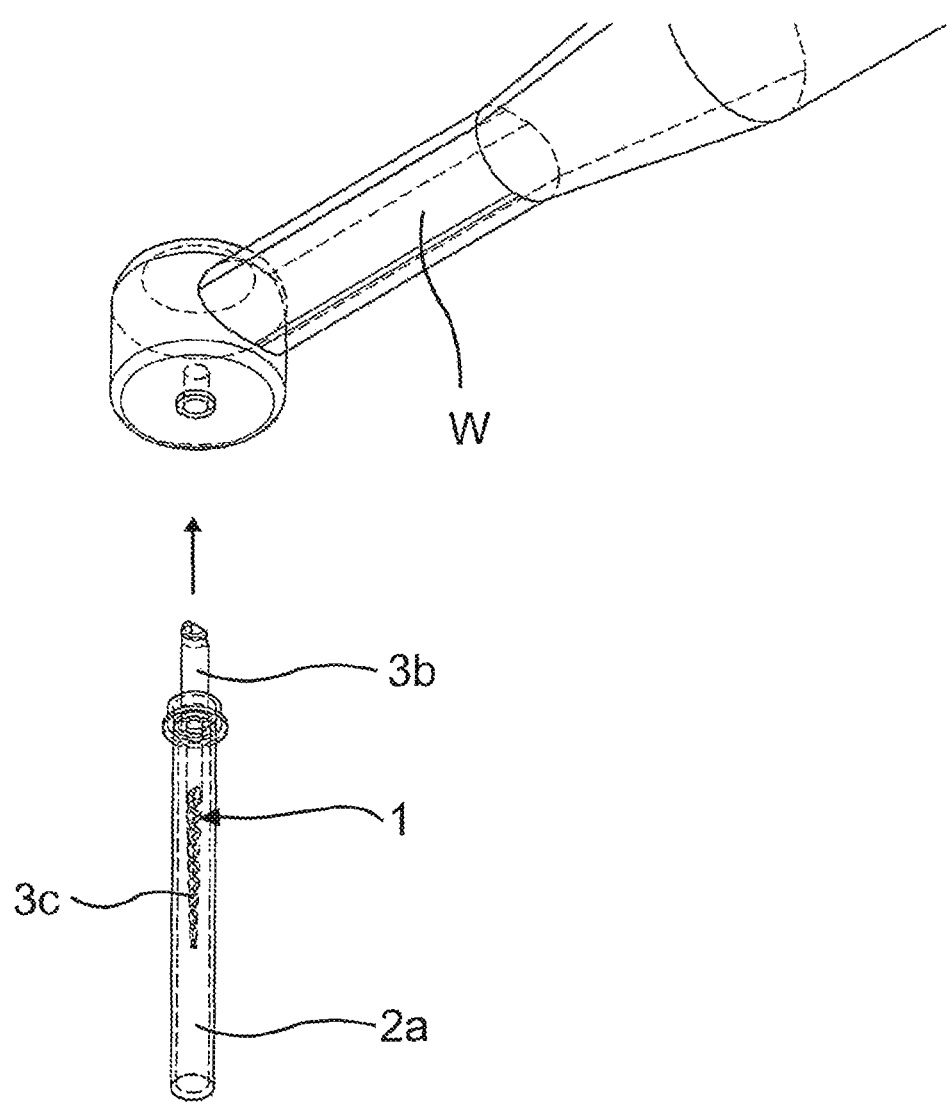

In the FIGS. 1 to 3 and FIGS. 4 to 6 two embodiments of a kit according to the invention are shown, the kit consisting of an endodontic instrument 1 and a container 2 that is designed as a disposable package, in which the instrument 1 is stored in a sterile manner. The instrument 1 is designed as an endodontic file in both embodiments and has a tool shaft 3, on one upper axial end region of which a handle 3a (FIGS. 1 to 3), or alternatively a coupling section 3b for connection to a motor-driven rotary tool (see versions of FIGS. 4 to 6) is formed and on the other, lower end region of which a conically tapering working section 3c is formed.

The coupling section 3b of the instrument 1 is particularly preferably provided by a shaft according to DIN EN ISO 6360-1 or includes such a shaft.

The receptacle 2 for storing the instrument 1 is of tubular shape and has a lower container part 2a that is open on its top side and an upper container part 2b that is open on its underside, which is plugged into the lower container part 2a. For the axial positioning of the upper container part 2b, an outwardly projecting stop flange 4 is formed on the lower container part 2a, against the upper side of which the lower end face of the upper container part 2b comes into contact. The plug connection therein is designed such, that the upper container part 2b cannot detach from the lower container part 2a by itself but instead the upper container part 2b must be pulled of the lower container part 2a in order to open the container 2.

As shown in particular in FIG. 1, the arrangement is configured such, that the working section 3c of the endodontic instrument 1 is accommodated in the lower container part 2a and the upper axial end section with the handle 3a/coupling section 3b is accommodated in the upper container part 2b.

In order to position the endodontic instrument 1 in the container 2, a holder 5 is provided in the region of the open upper side of the lower container part 2a, which comprises a central axial through-opening 6, through which the working section 3c of the instrument 1 is inserted in the lower container part 2a. The holder 5 is designed as a plastic ring, which is pressed into the lower container part 2a, so that the lower container part 2a is closed by the holder 5, except for the area of its central through-opening 6. The central through-opening has the size adapted to the diameter of the tool shaft 3, so that the instrument 1 is radially positioned in the holder 5 and is smoothing clamped. Furthermore, the arrangement is configured such, that the instrument 1 is also positioned axially in the holder 5 in its inserted state. In the design examples shown in the drawing, axial stop surfaces are provided on the lower container part 2a and/or the holder 5 for this purpose against which the underside of the handle 3a/coupling section 3b of the endodontic instrument 1 comes into contact.

According to the invention, the container 2 is made of a plastic material, which is so rigid that it is hardly or only imperceptibly deformed when the lower container part 2a is gripped in order to release the upper container part 2b from it and to pull out the endodontic instrument 1. In this way, it is possible to remove the instrument 1 from the container 2 and optionally connect it to a motor-driven rotary tool without having to touch the working section 3c of the instrument 1. The plastic material of the container 2 therein is selected such, that it is transparent to a sterilizing radiation and is also not affected by it. In this way, it is possible to sterilize the instrument 1 after having inserted it in the container 2. Accordingly, a sterilization in the practice before the treatment is not necessary.

In a further design not shown in the drawings it is provided that the lower container part 2a and/or the upper container part 2b comprise an opening, which is closed by a sterilizing membrane that can be pierced in order to introduce a gaseous or vaporous fluid, in particular hydrogen peroxide, peracetic acid and/or dissolved ozone into the container for sterilization, wherein the sterilizing membrane is pierced by the needle and self-closes after the removal of the needle. In this case, a gaseous and/or vaporous fluid, such as for example hydrogen peroxide, peracetic acid and/or dissolved ozone can be introduced into the lower container part and/or the upper container part, for which purpose the corresponding sterilization membrane is pierced. The sterilization membrane therein is self-closing, so that the piercing opening of the needle closes itself again after the needle has been pulled out. This design is particularly useful, if an endodontic instrument 1 is to be reused after cleaning. The sterilization membrane can also be designed in such a way that it is permeable to a vaporous or gaseous sterilization fluid (e.g. such rated steam or air) at the high temperatures prevailing during sterilization in an autoclave, usually >121° C., but is self-closing at room temperature.

Furthermore, in a manner not shown, optical markings are provided on the top side of the containers 2, which correspond to the type and/or size of the endodontic instruments stored in them.

Figure 8:
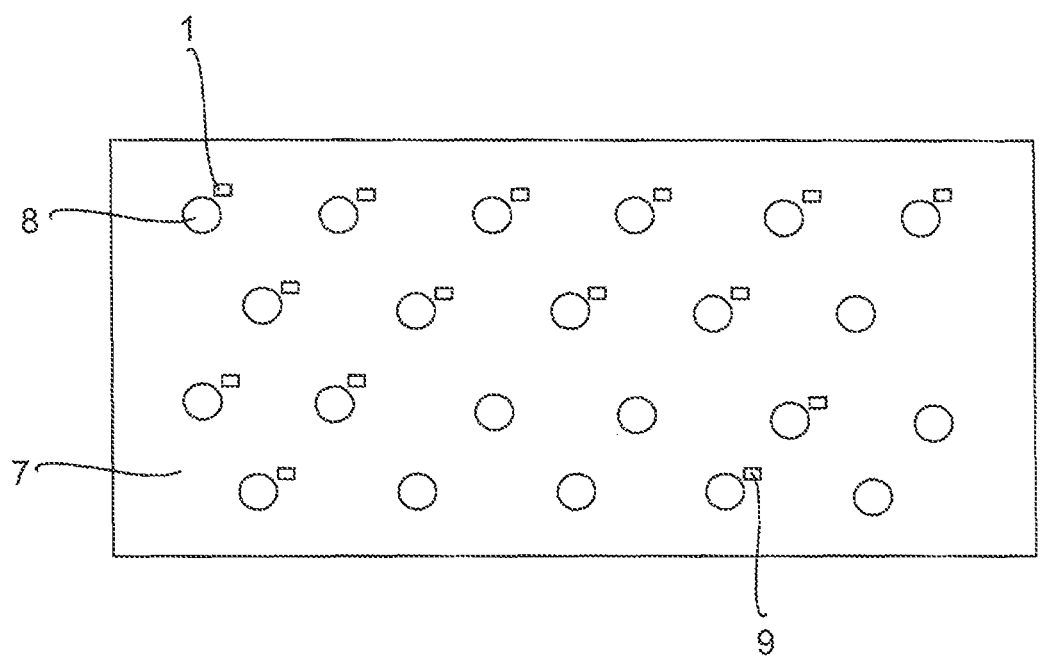

The rigidity of the tubular containers allows for them to be stored in a setting box 7, such as shown in FIG. 8. The setting box 7 is provided with appropriate receptacles 8, in which the containers 2 can be positioned next to another and in an upright position. Each receptacle 8 of the setting box 7 is provided with an optical marking 9, which indicates the type and/or size of the endodontic instrument 1 to be stored therein. Because of the easy recognition of the optical markings on the containers 2 on one hand and on the setting box 7 on the other hand, an easy allocation is possible. Through the optical markings 9 on the setting box 7 it is further possible to automatically recognize, which endodontic instruments 1 are missing in the setting box 7 after a treatment.

Figure 9:
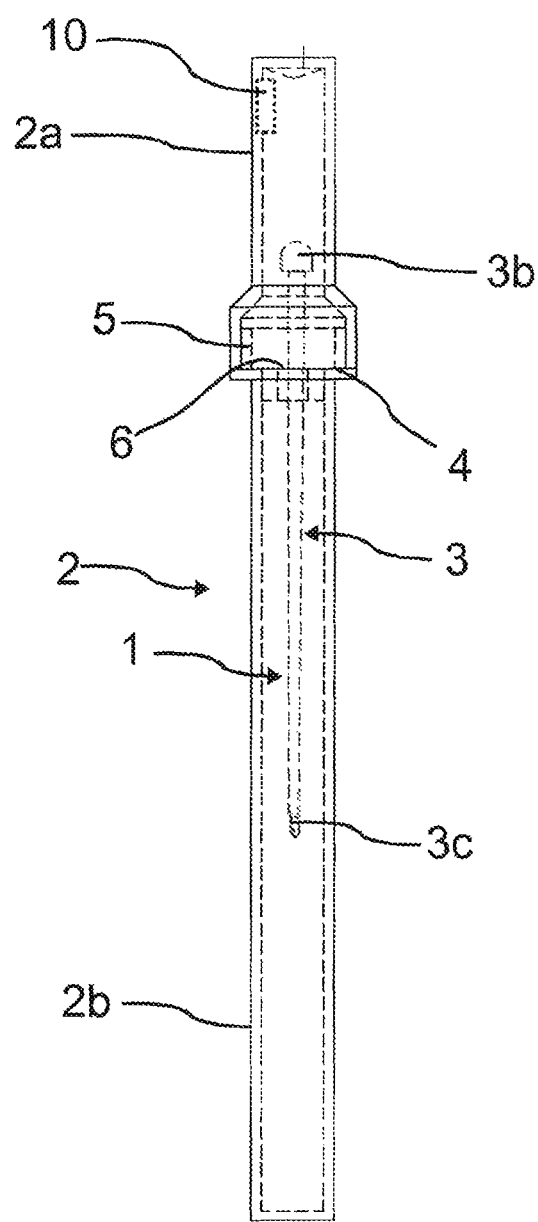
Figure 10:
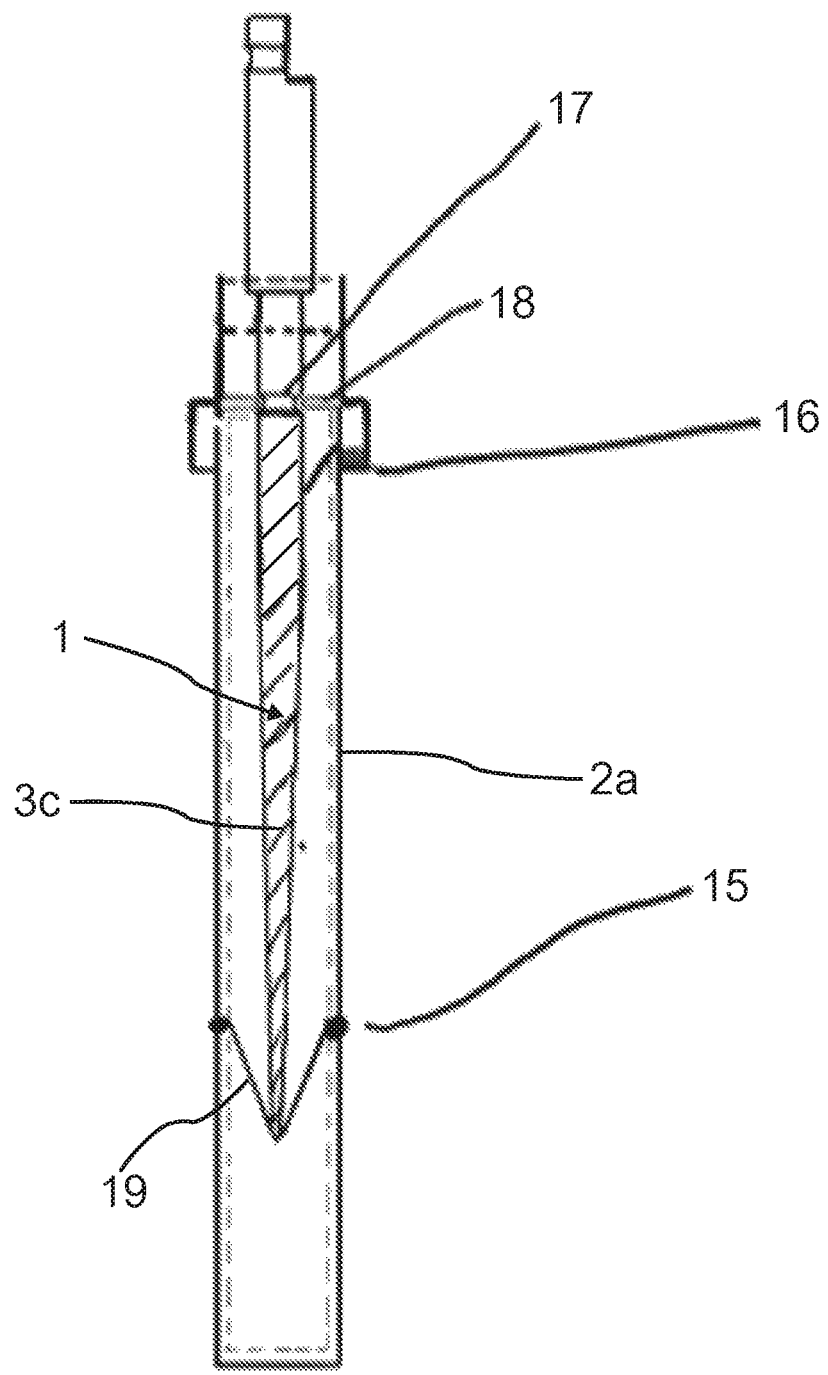

The FIGS. 9 and 10 show schematic representations of embodiments of kits according to the invention. Therein, the container 2 is in each case is characterized by the same structure as described above in connection with the first two examples. In particular, these also have an upper container part 2b and a lower container part 2a, a stop flange 4 and a holder 5 with a central through-opening 6. Identical components are marked with identical reference signs.

In the case of the containers 2 of the kits according to the FIGS. 9 and 10, the lower container part 2a is in each case designed for receiving the working section of the corresponding dental instrument and the upper container part 2a is in each case configured for receiving the upper axial end region of the corresponding endodontic instrument, which in particular comprises a shaft according to DIN EN ISO 6360-1, or consists of such a shaft.

The kit shown in FIG. 9 differs from the kits explained above in that its container 2 is equipped with a transmitting and receiving device 10 that is attached to the inside of the upper container part 2a. As one can see, the transmitting and/or receiving device 10 is partially recessed into the wall of the upper container part 2a of the container 2 and/or inserted into a recess in the wall.

In the design example shown, the transmitting and receiving device 10 is provided in the form of an RFID-chip, which can wirelessly receive and transmit data and/or information as well as send it and on which information can be stored. In the present case, information regarding the dental instrument 1 received in the container 2 are stored in the transmitting and receiving device 10, specifically a code for identifying the instrument.

It should be noted that a transmitting and receiving device 10 may be provided both instead of or in addition to an optical marking on the container 2.

Data stored on the transmitting and receiving device 10 can be read out via the recorded instrument 1 by means of a suitable reader device or reader-and-writer device that is not shown in the Figures and can then, for example, be—in particular automatically—passed on to a management system/program (praxis management program, merchandise management system).

Thereby, an accurate and automated control, inventory and ordering is enabled. In combination with patient and treatment data, it is further possible to ensure traceability of patient and/or treatment and/or operation allocation.

Further, information regarding the batch documentation (lot-number) of the received endodontic instrument 1 can be stored on the transmitting and receiving device 10. A management system can use the sterilization and/or expiration dates to warn against the use of expired instruments. Further, in the manufacturing and production area it is also used for an integration into an ERP (enterprise resource planning) software system.

As a result, advantages for the merchandise management system as well as ERP systems can be attained and reliable traceability of medical devices can be achieved.

If one or more kits with containers 2, which have a transmitting and receiving device 10, are used together with a setting box 7, any reader device or reader-and-writer device can also be provided on the setting box 7, in particular be built into it, which is not shown in the Figures.

It is emphasized that, in analogy to the design example according to FIG. 9, the containers 2 of all the design examples can also be equipped with a transmitting and receiving device 10.

FIG. 10 shows a fourth embodiment of the container 2 according to the invention with an inserted endodontic file 1, wherein only the lower container part 2a of the container 2 is visible. In contrast to the previous embodiments, the endodontic file 1 is not fixed in the lower container part 2a in a clamping manner, but by means of a latching connection and is positioned radially. For this purpose, the tool shank 3 has an annular circumferential latching groove 17, with which latching means that are provided on the lower container part 2a in the form of a plurality of latching tongues 18 that are provided along the circumference of the lower container part 2a are in latching engagement.

Furthermore, the lower container part 2a is provided with means for determining the state of use and/or the degree of wear of the working section 3c of the endodontic instrument 1 inserted into the lower container part 2a. These means are provided to determine the electrical conductivity or the electrical resistance of the working section 3c and for this purpose have electrical contacts 15, 16, which are in electrical contact with the working section 3c inserted in the lower container part 2a at an upper and a lower end region of it. In the present design, the electrical contacts are provided at the lower end region of the lower container part 2a and on the underside of the stop flange 4 of the lower container part 2a. The upper electrical contact 16 is electrically connected to the latching tongues 18, which consist of an electrically conductive material and are in contact with the tool shaft 3. The lower electrical contacts 15 are designed in order to come into engagement with the tip of the working section 3c. For this purpose, an electrically conductive and elastically designed membrane is provided, which spans the cross-section of the lower container part 2a.

The lower container part can be connected to an electrical circuit via the electrical contacts 15, 16, so that the electrical current flows through the working section 3c. In the electric circuit, display means that are not shown are provided, which show the state of use on the basis of the resistance of the working section 3c detected with respect to its electrical conductivity. Here, it is taken into account, that the endodontic file is subjected to structural changes, especially in the form of settlements, in particular due to repeated bending processes in the curved dental root canal, which lead to a change in electrical conductivity.

Figure 11:
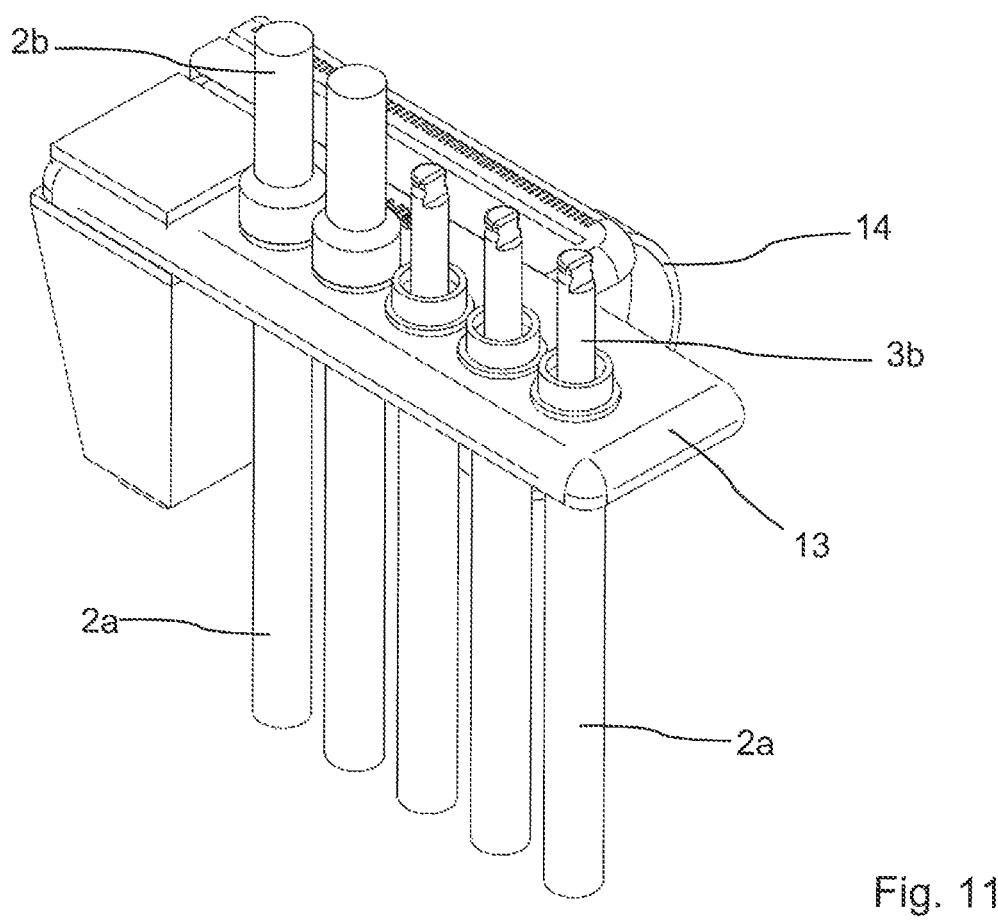
Figure 12:
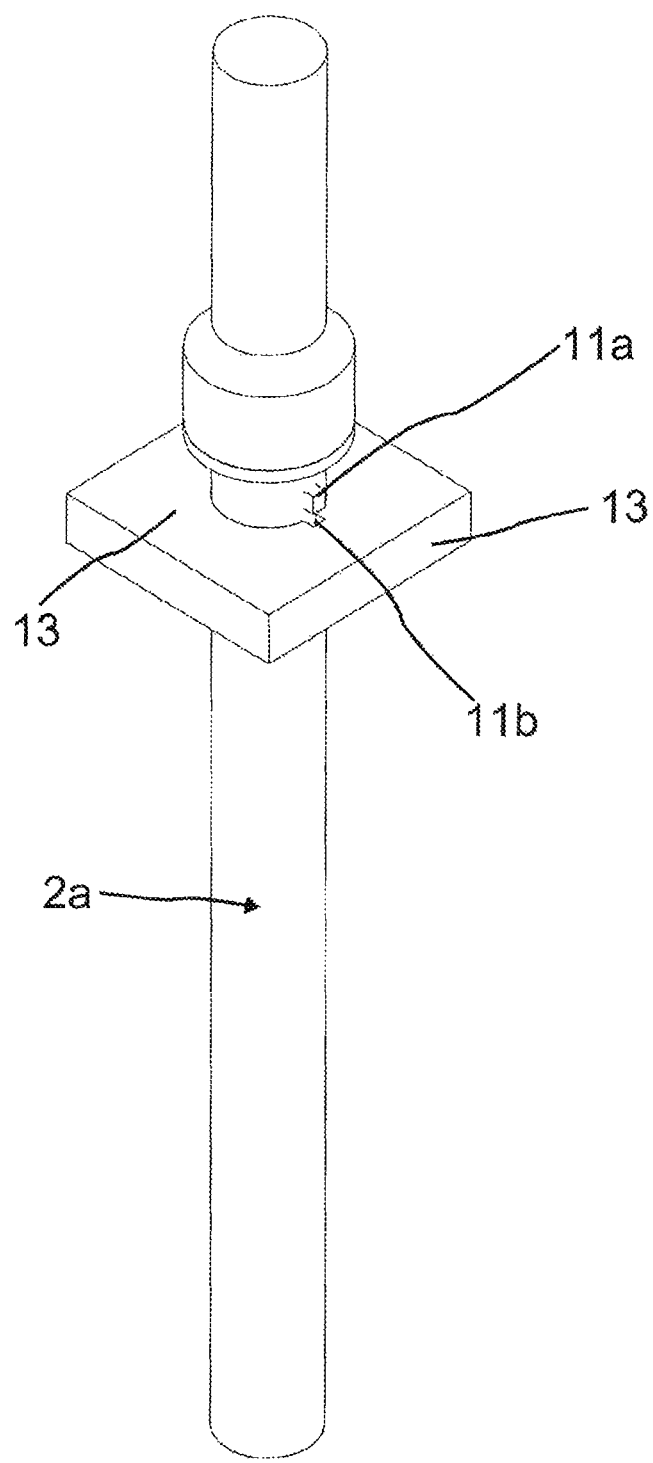
Figure 13:
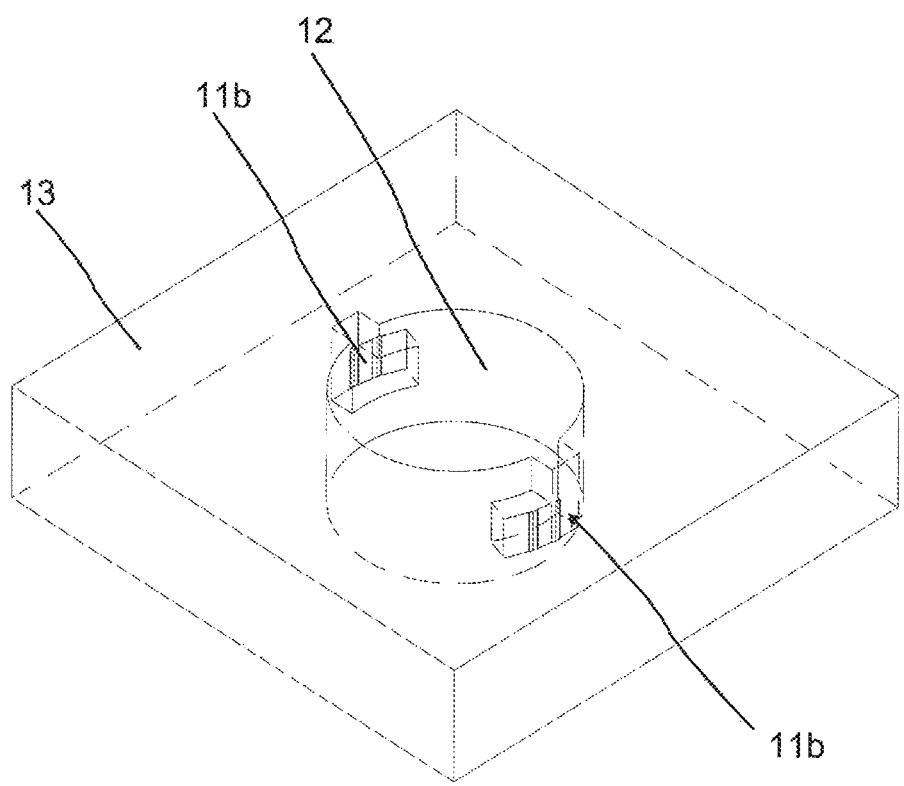

It is advisable, to provide a holding box on the dentist's chair with the endodontic instruments that are required for the planned procedure. Such a holding box 13 for five endodontic instruments is shown in FIG. 11. Here, it can be seen that the holding box 13 has five receptacles 12, in which the containers 2 of the kit according to the present invention are inserted. In order to fix the containers 2 in the holding box 13 in a secure manner, corresponding fastening means are provided on the outside of the containers and the insides of the receptacles 12. For example, the containers 2 can be screwed into the receptacles. Alternatively, however, a bayonet lock can be provided. The FIGS. 12 and 13 show such a design, in which the corresponding male bayonet catch parts 11a, also called nocks, are formed on diametrically opposite sides of the lower container part 2a and the corresponding bayonet holders 11b are provided in the holding box 13 in the region of the receptacles 12. This type of attachment allows for the required endodontic instruments to be transported and stored fixed in the holding box 13. In addition, the upper container parts 2b can be removed from the lower container parts 2a with one hand, if the holding box is appropriately fixed at the dentist's workplace, for which purpose the holding box 13 in FIG. 13 has a corresponding fastening section 14.

The invention claimed is:

1. A kit, comprising:
   a single endodontic instrument (1) in the form of an endodontic file, which has a tool shaft (3), a handle or a coupling section formed on an upper axial end region of the tool shaft (3) for connection to a motor-driven rotary tool, and a working section (3c) formed on a lower axial end region of the tool shaft (3); and
   a container (2) designed as a disposable packaging for storing the single endodontic instrument (1) and having a lower container part (2a), which is open at a top side thereof for receiving the working section (3c) of the single endodontic instrument (1), and has an upper container part (2b), which is open at an underside thereof for receiving the upper axial end region of the single endodontic instrument (1),
   wherein a holder (5) is provided on the top side of the lower container part (2a), the holder (5) having an axial through-opening (6) through which the working section (3c) of the single endodontic instrument (1) is inserted into the lower container part (2a), wherein the tool shaft (3) of the instrument (1) is positioned at least one of radially and axially in the through-opening (6) and is fixed in at least one of a clamping manner and by a latching connection, wherein the upper container part (2b) is connected to the lower container part (2a) in an airtight manner to form the container (2), and wherein an interior of the container (2) and the single endodontic instrument (1) are sterile, and wherein at least the lower container part (2a) consists of a material dimensionally stable in such a way that the single endodontic instrument (1) inserted into the lower container part (2a) and positioned in the holder (5) can be gripped at the upper axial end region thereof and pulled out of the lower container part (2a) while being held manually without the lower container part (2a) being deformed by the holding pressure to such an extent that it comes into contact with the working section (3c).

2. The kit according to claim 1, wherein the lower container part (2a) consists of a dimensionally stable material in such a way that the lower container part (2a) is not or only imperceptibly deformed by the manual holding pressure when an instrument (1) is pulled out.

3. The kit according to claim 1, wherein the upper container part (2b) consists of the same material as the lower container part (2a) or a material of similar dimensional stability as the lower container part (2a).

4. The kit according to claim 1, wherein the lower container part (2a) and/or the upper container part (2b) are made of a plastic material and/or have a magnifying area and/or a lens area.

5. The kit according to claim 1, wherein the lower container part (2a) and/or the upper container part (2b) consist of a material that is transparent to sterilizing radiation and/or of a material, which is transparent to a sterilization gas.

6. The kit according to claim 1, wherein the lower container part (2a) and/or the upper container part (2b) has an opening, which is closed by a sterilizing membrane and which can be pierced through order to introduce a gaseous or vaporous fluid, in particular hydrogen peroxide, peracetic acid and/or dissolved ozone into the container (2), wherein the sterilizing membrane is pierced by a needle and self-closes after removal thereof.

7. The kit according to claim 1, wherein the container (2) is formed as a tube.

8. The kit according to claim 1, wherein the upper container part (2b) and the lower container part (2a) are plugged together, and wherein the plug connection between the lower container part (2a) and the upper container part (2b) is designed to be airtight.

9. The kit according to claim 1, wherein a sealing strip is provided and/or the connection between the lower container part (2a) and the upper container part (2b) is sealed to seal a gap between the lower container part (2a) and the upper container part (2b) in the transition region between the lower container part (2a) and the upper container part (2b).

10. The kit according to claim 1, wherein the holder (5) completely closes the open top side of the lower container part (2a) with exception of the axial through opening (6).

11. The kit according to claim 1, wherein the holder (5) consists of an elastic plastic material.

12. The kit according to claim 1, wherein fastening means are formed on the outside of the container (2) in order to fix the container (2) in a receptacle (12) of a holding box (13) or a setting box.

13. The kit according to claim 1, wherein a transmitting and/or receiving device (10) is provided, which is configured to transmit and/or receive information about the single endodontic instrument (1) that is accommodated by or can be accommodated by the container (2.

14. The kit according to claim 13, wherein information about the single endodontic instrument that is accommodated or can be accommodated by the container (2), can be stored or is stored in the transmitting and/or receiving device (10).

15. The kit according to claim 1, wherein means for determining at least one of the state of use and the degree of wear of the working section (3c) of the single endodontic instrument (1) inserted into the lower container part (2b) are provided on the lower container part (2a) and/or the holder (5), wherein the means are connected or can be connected with a display unit in order to display the state of use and/or the degree of wear, and wherein the means are designed to determine at least one physical property of the working section (3c).

16. The kit according to claim 15, wherein the means for determining the state of use and/or degree of wear of the working section (3c) are configured to determine the electrical conductivity/resistance of the working section (3c) and comprise electrical contacts (15, 16), which are in electrical contact with the working section (3c) inserted into the lower container part (2a) at an upper or a lower end region thereof and which are connected and can be connected to the display unit, wherein the electrical contacts are provided in the lower end region of the lower container part (2a) and on the underside of a stop flange (4) of the lower container part (2a), and wherein two upper electrical contacts (16) and two lower electrical contacts (15) are provided on the lower container part (2a), the electrical contacts are in electrical contact with the working section (3c).

17. The kit according to claim 16, wherein the holder (5) is designed to fix the tool shaft (3) of the single endodontic instrument (1) in the lower container part (2a) a latching connection, wherein the tool shaft (3) has a circumferential latching groove (17), wherein the latching connection is in the form of at least one annular latching tongue (18) provided along a circumference of the lower container part (2a) in latching engagement with the latching groove (17), and wherein the at least one annular latching tongue (18) touch the tool shaft (3), are designed to be electrically conductive and are electrically connected to the upper electrical contact (16).

* * * * *